United States Patent [19]
Cipullo

[11] Patent Number: 5,856,589
[45] Date of Patent: Jan. 5, 1999

[54] METHOD TO DEFOUL BISPHENOL-PHENOL ADDUCT FOULED CRYSTALLIZER COOLERS

[75] Inventor: Michael J. Cipullo, Prattville, Ala.

[73] Assignee: General Electric Company, Pittsfield, Mass.

[21] Appl. No.: 909,010

[22] Filed: Aug. 8, 1997

[51] Int. Cl.[6] .................................................. C07C 39/16
[52] U.S. Cl. ........................................... 568/728; 568/727
[58] Field of Search .................................... 568/727, 728; 510/405; 252/364

[56] References Cited

U.S. PATENT DOCUMENTS

| | | |
|---|---|---|
| 4,209,646 | 6/1980 | Gac . |
| 4,327,229 | 4/1982 | Mendiratta . |
| 4,950,806 | 8/1990 | Iimuro . |
| 5,243,093 | 9/1993 | Kissinger . |

FOREIGN PATENT DOCUMENTS 86-144743/19   3/1995   Japan .

*Primary Examiner*—Michael L. Shippen

[57] ABSTRACT

An improvement in the continuous preparation of a bisphenol comprising maintaining the efficiency of the adduct crystallizer. The improvement comprises maintaining the Delta-T of the crystallizer at less than about 4° C.

8 Claims, 2 Drawing Sheets

METHOD TO DEFOUL BISPHENOL-PHENOL ADDUCT FOULED CRYSTALLIZER COOLERS

BACKGROUND OF THE INVENTION

1. Field of the Invention

The invention relates to processes for the synthesis of dihydric phenols and more particularly to an improved process for recovering bisphenol-A.

2. Brief Description of Related Art

The dihydric phenol 2,2 bis(p-hydroxyphenyl) propane (commonly referred to as "bisphenol-A") is commercially prepared by condensing 2 moles of phenol with a mole of acetone in the presence of an acid catalyst. The phenol is present in a molar excess of the stoichiometric requirement. During the condensation, a number of by-products are formed which are contaminants of the desired product, bisphenol-A. These contaminants, carried in the product stream from the condensation reaction zone, include water, trace quantities of acidic materials derived from the catalyst, unreacted phenol and acetone and a number of isomers of bisphenol-A.

Conventionally, an early step in separating the desired bisphenol-A from the product stream may involve cooling the product stream to induce crystallization and precipitation of the bisphenol-A in the form of a 1:1 adduct with the excess of phenol present. The crystallized adduct is separated, washed, and the phenol removed by distillation, extraction or steam stripping.

In commercial plants for the synthesis of bisphenols, the production of the bisphenol-phenol adducts and delivery to crystallization coolers is generally continuous or semi-continuous. Over periods of time, the coolers will foul with precipitated adduct, reducing their efficiency. This fouling can occur every 4 to 8 weeks, requiring an interruption in their use for a procedure commonly referred to as "meltout". The procedure comprises passing hot phenol through the cooler system to melt out the deposits of crude bisphenol, which occurs mainly in the coolers.

An alternate procedure for defouling the coolers comprises heating both the coolers and the crystallizers with process solutions containing typically 5.0 to 26.0 percent bisphenol to remove the bisphenol deposits coating the inside of the coolers and the crystallizers. The cooling medium in the heat exchanger is also warmed during the meltout.

The time elapsing between meltouts is dictated-in-part by the efficiency of a preceding meltout and, in part, by operating conditions of the process reaction (rate of product delivery, etc.). The frequency of required meltouts affects, of course, the overall efficiency of a commercial process line and the ultimate cost of the desired bisphenol product.

Further, meltouts are at times not successful, when measured by the "Delta T" factor (temperature difference between the process solution and the cooling medium) which increases as the cooler becomes more fouled with bisphenol-phenol adduct on heat-exchanging surfaces.

We have now discovered that the efficiency of defouling coolers and crystallizers with hot phenol is improved substantially when the phenol contains a bisphenol solubilizing proportion of water. Fewer meltouts are required in a given time period, requiring fewer interruptions of continuous and semi-continuous synthesis of the desired bisphenol.

Water has previously been added to the bisphenol-phenol adduct of crystallization to improve adduct purity. However, the process as described in U.S. Pat. No. 4,950,806 (Imuro et al., 1990) requires a lower operating temperature due to the increased solubility of BPA. Other patents relating to water addition to adduct crystallization include U.S. Pat. No. 4,209,646 (Gac et al., 1980) describes BPA adduct crystallization with 2 to 20% water evaporative cooling. Japanese 83-135832 (Mitsui Toats Aug. 12, 1983) describes water addition to add crystals to control solution density and crystals. Japanese Patent JPO7069951-A recently issued to Idemitsu Petrochemical and Tsukishima Kikai Co. describes the use of phenol mixtures containing 1–20% water to reduce solids build-up in evaporative crystallization pipe through which the vaporized components pass. (Note that evaporative cooling involves the use of a vacuum and removal of water's heat of evaporization to cool and crystallize. In contrast, the present inventors use a separate cooling medium and shell and tube heat exchanger system to cool the process solutions.

SUMMARY OF THE INVENTION

The invention comprises an improved method of defouling a cooling and crystallization surface, fouled upon crystallization of a 1:1 adduct of phenol and bisphenol-A thereon, which comprises;

dissolving the adduct adhering on the surface with phenol containing from 3 to 40 weight percent of water.

DETAILED DESCRIPTION OF THE PREFERRED EMBODIMENT OF THE INVENTION

Figure 1:
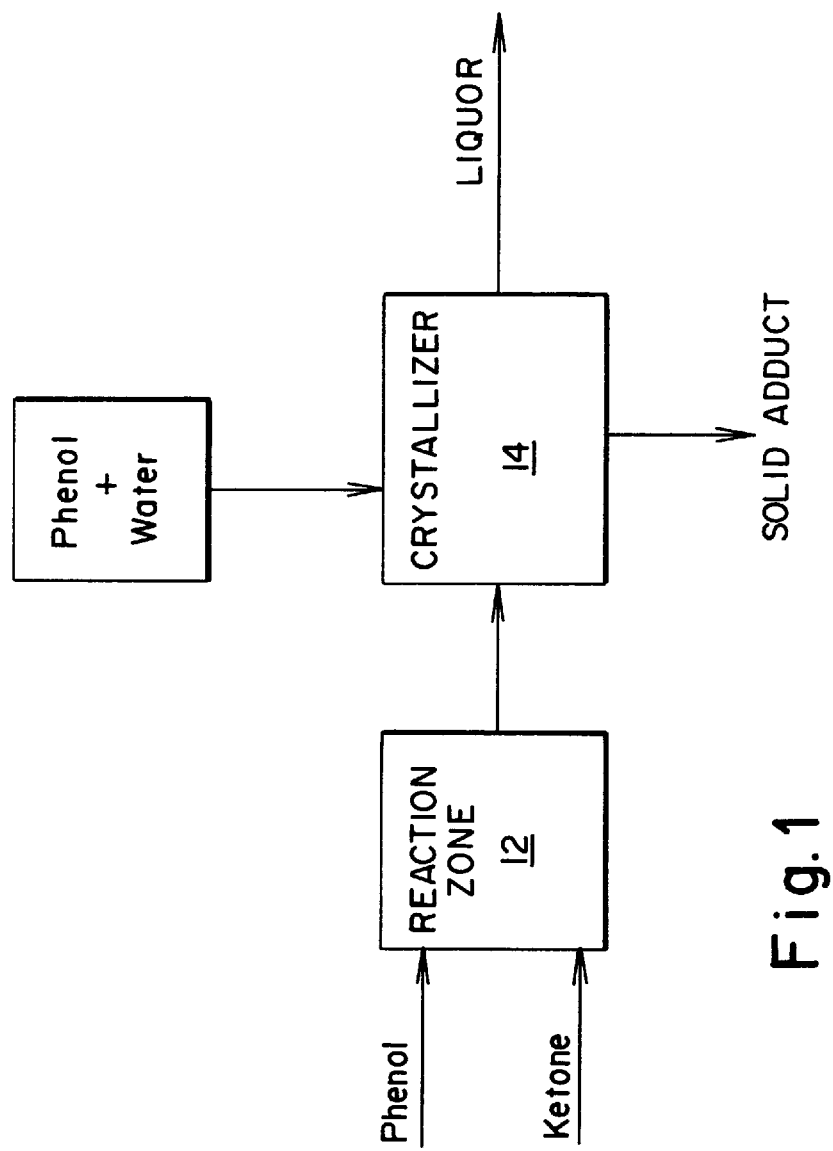
FIG. 1 is a block diagram representing a preferred embodiment of the invention.

As mentioned above, commercial processes are known for the production of bisphenols by condensation of phenols with ketones, the initial crude product being a 1:1 adduct of the phenol with bisphenol. In an initial separation/purification the adduct is crystallized from the product stream of the condensation. Representative of many literature descriptions are those found, for example, in the U.S. Pat. No. 4,051,079 (Melby) U.S. Pat. No. 4,950,806 (Imuro et al.); and U.S. Pat. No. 5,243,093 (Kissinger et al.), all incorporated herein by reference thereto. The majority of commercial processes are designed for continuous production, the adduct being present in the product stream flowing from the condensation reaction zone.

With reference to the accompanying drawing of a block diagram showing a portion of the commercial production of bisphenol, a molar excess of phenol is delivered to a reaction zone 12 with a ketone such as acetone. The condensation of the two reactants occurs continuously in reaction zone 12.

The reaction temperature in the reactor zone 12 may vary from 40° C. to 95° C. with reaction temperatures in the range of from 55° C. to 90° C. being preferred.

The reaction time in the reactor zone 12 may vary and depends on reaction temperature. For example, the liquid hour space velocity (LHSV) of the feed may vary between wide limits with velocities in the range of from 0.2 to 40 liters feedstream/liter catalyst$^{-1}$/hour$^{-1}$.

The reaction zone 12 effluent is continuously withdrawn and fed to a system for separation of the product bisphenol- A. This effluent comprises unreacted phenol, unreacted acetone, acid residues of the catalyst, water and isomers of bisphenol-A in admixture with the desired bisphenol-A. The isomers and by-products of interest are compounds wherein the hydroxy groups are not in the para configuration relative to the isopropylidine group. It is this effluent which may provide a starting material for the method of the present invention. The effluent may be treated first by cooling to precipitate a crystalline 1:1 adduct of bisphenol-A with phenol, and separating the solid adduct in a crystallizer 14. When the cooler surfaces in crystallizer 14 accumulate a deposit of the crystallized 1:1 adduct, crystallizer efficiency degrades. Ideally, the Delta-T of the cooling surface is a less than about 4° C. The Delta-T is as mentioned above the temperature difference between the process solution and the cooling surface.

It cannot be stressed enough to maintain Delta-T less than 4°. Having done this many times in a jacketed glass crystallizer, one can watch the nucleation, and vice versa, the erosion of build-up on the cool surface as the temperature is raised and lowered around the 4° Delta.

The following example and preparations describe the manner and process of making and using the invention and set forth the best mode contemplated by the inventor of carrying out the invention but are not to be construed as limiting the invention.

Lab Procedure

The following series of experiments were completed to determine the BPA solubility curves in phenol/water in the range of 5 to 40% water in phenol.

Add phenol and water as listed in the following table to a 250 ml flask.

TABLE

| experiment number | grams of water | grams of phenol | resulting % water in phenol | Grams of BPA dissolved per 100 grams of solution at 60° C. |
|---|---|---|---|---|
| 1 | 5 | 95 | 5% | 18 |
| 2 | 10 | 90 | 10% | 31 |
| 3 | 20 | 80 | 20% | 45 |
| 4 | 30 | 70 | 30% | 85 |
| 5 | 40 | 60 | 40 | >125 |

2) In each experiment add 5 grams of BPA, heat until homogeneous on a heated stir plate also with the aid of a heat gun as needed.

3) Cool with shaking, recording the exact temperature where cloudiness and crystallization begins.

4) Repeat steps 2 and 3 in each experiment adding between 5–20 grams of BPA each time. The data is collected using the total amount of BPA present in the flask.

Figure 2:
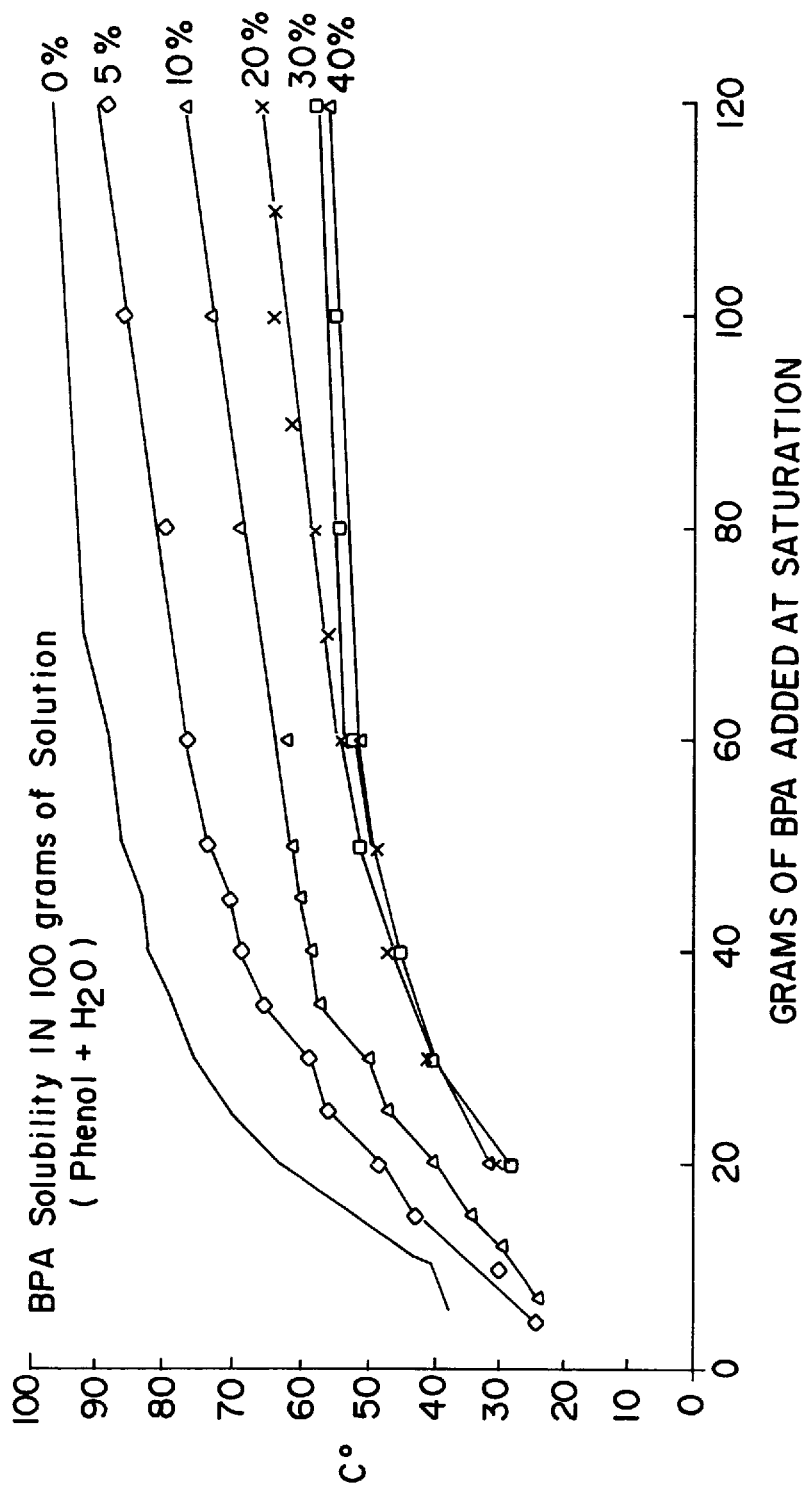
FIG. 2 is a graphical representation of the data obtained from a series of experiments to determine the solubility of BPA in solution of water in phenol.

The resulting BPA solubility curves (BPA vs temperature) show water/phenol mixtures will dissolve more BPA compared to pure phenol at higher temperatures; see the graphical representation of FIG. 2.

The use of phenol/water mixtures during meltout or intermittently between meltouts should reduce the time needed for a meltout or the frequency of required meltouts. There are several options on how this invention can be practiced commercially, including but not limited to the following:

1) Crystallizer circulation can be stopped, process solutions can then be drained from the cooler, and replaced with a hot phenol/water solution, and the shell side of the exchanger heated with steam to aid meltout of BPA adduct (and any by-products present). Agitation can he provided to increase efficiency.

2) The crystallizer circulation can be stopped, process solution drained from the cooler and replaced with Phenol with injection of steam into the phenol to increase the temperature and water content as well as proved some agitation. Steam can also be added to the shell side of the cooler.

3) The crystallizer circulation can be stopped briefly and either phenol/water or phenol/steam or just steam can be injected directly into the process solution in the cooler (containing Phenol/BPA/by-products and some water). The shell cooling medium can be turned off or warmed during this procedure. While this procedure briefly inhibits the crystallization process, carrying out this option intermittently to reduce buildup can avoid actual shutdown of the line and significantly extend the time required between cooler meltouts. This eliminates downtime providing an increase in annualized production.

The added phenol/water or steam is compatible with the present process. They will pass through the crystallizer and adduct filter into the mother liquor. From there the water can be removed by distillation (along with water formed in reaction). Any added phenol is also raw material which will be converted to BPA upon recycle to reaction.

The examples have shown that water levels between 5 and 40% in phenol provide the increased BPA solubility relative to pure phenol.

What is claimed is:

1. An improved method of defouling a cooling and crystallization surface, which comprises:

crystallizing a 1:1 adduct of phenol and bisphenol-A in crystallizer until unacceptable fouling occurs; and dissolving the adduct adhering on the cooling and crystallization surface with phenol containing from 5 to 40 weight percent of water.

2. The method of claim 1 wherein said dissolving step is carried out at a temperature of about 40° to 90° C.

3. The method of claim 1 wherein said crystallization step is carried out in a process for continuous production of bisphenol.

4. A method of continuously preparing a bisphenol, which comprises:

condensing a ketone with a phenol in the presence of a molar excess of the phenol whereby a reaction product is obtained containing a 1:1 adduct of a bisphenol and the phenol; and separating the adduct from the reaction product by crystallization; and maintaining Delta-T of the crystallizer at less than about 4° C. by dissolving the adduct adhering to the crystallizer cooling surfaces in a phenol water solution containing 5 to 40 percent v/v water.

5. The method of claim 4 wherein the phenol/water solution is at a temperature of about 40° to 90° C.

6. The method of claim 4 wherein the phenol/water solution or steam is introduced into the crystallizer with the reaction product.

7. The method of claim 4 wherein the phenol/water solution or steam is introduced into the crystallizer sequentially following the reaction product.

8. The improved method of claim 4 wherein the bisphenol is bisphenol-A.

* * * * *